(12) United States Patent
Patzer et al.

(10) Patent No.: US 12,090,311 B2
(45) Date of Patent: Sep. 17, 2024

(54) PUMP CATHETER FOR THE DIRECTED PULSATILE CONVEYING OF BLOOD

(71) Applicant: NovaPump GmbH, Jena (DE)

(72) Inventors: Patrick Patzer, Harth-Poellnitz (DE); Joerg Pfeifer, Jena (DE); Ronald Reich, Jena (DE)

(73) Assignee: NovaPump GmbH, Jena (DE)

( * ) Notice: Subject to any disclaimer, the term of this patent is extended or adjusted under 35 U.S.C. 154(b) by 970 days.

(21) Appl. No.: 16/994,194

(22) Filed: Aug. 14, 2020

(65) Prior Publication Data

US 2020/0376179 A1 Dec. 3, 2020

Related U.S. Application Data

(63) Continuation of application No. PCT/EP2019/052953, filed on Feb. 6, 2019.

(30) Foreign Application Priority Data

Feb. 14, 2018 (DE) .......................... 102018103364.8

(51) Int. Cl.
| | |
|---|---|
| *A61M 60/13* | (2021.01) |
| *A61M 60/135* | (2021.01) |
| *A61M 60/148* | (2021.01) |
| *A61M 60/165* | (2021.01) |
| *A61M 60/295* | (2021.01) |
| *A61M 60/497* | (2021.01) |

(Continued)

(52) U.S. Cl.
CPC .......... *A61M 60/148* (2021.01); *A61M 60/13* (2021.01); *A61M 60/135* (2021.01); *A61M 60/165* (2021.01); *A61M 60/295* (2021.01); *A61M 60/497* (2021.01); *A61M 60/562* (2021.01); *A61M 60/585* (2021.01); *A61M 60/857* (2021.01); *A61M 60/894* (2021.01); *A61M 2205/0266* (2013.01)

(58) Field of Classification Search
CPC .. A61M 1/1041; A61M 1/1098; A61M 1/125; A61M 1/1008; A61M 1/1037; A61M 1/106; A61M 1/122
See application file for complete search history.

(56) References Cited

U.S. PATENT DOCUMENTS

| | | | |
|---|---|---|---|
| 5,891,012 | A | 4/1999 | Downey et al. |
| 8,409,128 | B2 | 4/2013 | Ferrari |

(Continued)

FOREIGN PATENT DOCUMENTS

| | | |
|---|---|---|
| DE | 102014003153 A1 | 9/2015 |
| DE | 102014012850 A1 | 3/2016 |

(Continued)

OTHER PUBLICATIONS

International Search Report dated May 13, 2019 of international application PCT/EP2019/052953 on which this application is based.

*Primary Examiner* — Jon Eric C Morales

(74) *Attorney, Agent, or Firm* — Walter Ottesen, P.A.

(57) ABSTRACT

A pump catheter for the directed pulsatile conduction of blood includes a proximal section and a distal section which has an expandable pump chamber and a tube section arranged distally from the pump chamber. The tube section has an outlet opening. An inlet element having at least one inlet opening is arranged between the proximal section and the pump chamber and the inlet element and the pump chamber are geometrically spaced apart by a coupling element.

13 Claims, 4 Drawing Sheets

(51) Int. Cl.
*A61M 60/562* (2021.01)
*A61M 60/585* (2021.01)
*A61M 60/857* (2021.01)
*A61M 60/894* (2021.01)

(56) References Cited

U.S. PATENT DOCUMENTS

| | | |
|---|---|---|
| 8,932,246 B2 | 1/2015 | Ferrari |
| 10,512,714 B2 | 12/2019 | Pfeifer et al. |
| 2017/0056574 A1 | 3/2017 | Pfeifer et al. |

FOREIGN PATENT DOCUMENTS

| | | |
|---|---|---|
| WO | 0035515 A1 | 6/2000 |
| WO | 2008113785 A2 | 9/2008 |

PUMP CATHETER FOR THE DIRECTED PULSATILE CONVEYING OF BLOOD

CROSS REFERENCE TO RELATED APPLICATION

This application is a continuation application of international patent application PCT/EP2019/052953, filed Feb. 6, 2019, designating the United States and claiming priority from German application 10 2018 103 364.8, filed Feb. 14, 2018, and the entire content of both applications is incorporated herein by reference.

FIELD OF THE INVENTION

The present invention relates to a pump catheter for the directed pulsatile conduction of blood. The catheter includes a proximal section and a distal section. The distal section includes an expandable pump chamber and a tube section arranged distally from the pump chamber. The tube section has an outlet opening.

BACKGROUND OF THE INVENTION

Catheters of the kind mentioned at the start are known as prior art, for example from U.S. Pat. Nos. 8,409,128; 8,932,246; US 2017/0056574 and U.S. Pat. No. 10,512,714. Such catheters are preferably placed in the human body percutaneously—for example via a groin-vessel opening—with the aid of established catheter technology for temporary support of the heart and circulation in the event of acute limited cardiac output or heart failure. In particular, it can also be used in the event of a relatively extreme aortic insufficiency. It is used to transport the body fluid to be conducted from a first site to another site without significantly increasing the pressure of the fluid at the first site beyond the physiologically specified state by realization of the principle of a submersible pump and combination thereof with the principle of a diaphragm pump, preferably by use of a balloon catheter.

A critical variable of such generic conduction catheters is the amount of blood that can be conducted through the catheter per unit of time. This should be as large as possible with, at the same time, minimum stress on sensitive blood constituents.

SUMMARY OF THE INVENTION

It is therefore an object of the invention to provide a catheter of the kind mentioned above that has an improved configuration in relation to prior known pump catheters.

The pump catheter of the invention is for the directed pulsatile conduction of blood. The pump catheter includes: a proximal section; a distal section including an expandable pump chamber and a tube section disposed distally of the expandable pump chamber; the tube section defining an outlet; an inlet element having at least one inlet opening and being arranged between the proximal section and the pump chamber; and, a coupling element geometrically spacing the inlet element and the pump chamber from each other.

In the context of the invention, "distal" means "toward the catheter end inserted into the body". In the context of the invention, "proximal" means "away from the distal catheter end". Thus, in the case of the catheter according to the invention, a proximal catheter end is arranged opposite to the distal catheter end and, when the catheter has been inserted into the body as intended, generally protrudes therefrom.

The multipiece structure of the catheter with an inlet element at a spatial distance from the pump chamber realizes advantages over the solutions known today in terms of fluid dynamics. The shear forces occurring by in the case of pulsatile impetus of abnormally viscous liquids such as, for example, human blood are minimized by the structure according to the invention and what is made possible is a laminar and calmed flow in the catheter interior. In this connection, the coupling element arranged between the pump chamber and the inlet element forms a flow-influencing factor.

Unlike in the case of prior known pump catheter concepts which provide inlet openings in the region of the pump chamber, the geometric separation of the inlet openings from the pump chamber means that the inlet element can be anatomically favorably configured independently of the pump chamber, this distinctly improving the take-up of blood into the catheter in comparison with inlet openings arranged on the outer wall of the pump chamber in a distributed manner.

It is important to transport blood as gently as possible. The invention can minimize current disadvantages of percutaneously placeable, temporary heart pumps, such as, for example, increased hemolysis rates and the associated tendency toward formation of thrombocytes. Furthermore, friction losses are minimized. This has advantages with regard to an increased pulsatile pump performance.

The proximal section of the catheter serves for the manipulation and the correct placement of the distal functional section in the patient. The proximal section is tubular. Preferably, supply lines communicating with structures of the distal part run through the tube lumen of the proximal part. The proximal section is, firstly, sufficiently flexible to largely adapt to a patient's anatomy during implantation of the catheter into the patient and, secondly, sufficiently rigid to allow feeding of the distal section to its intended site within the patient.

The distal section including the inlet element acts as a blood pump and is configured to conduct blood from a first site to a second site. Preferably, the catheter is intended for support of the pump performance of the right side of the heart. In this case, the catheter is, with the distal section out in front, fed into the patient's body as far as the right side of the heart via an access point in the groin, as far as the intended position thereof in the patient's body. In this position, the distal catheter section completely extends through the right side of the heart. It is intended that the inlet element containing the inlet opening and the pump chamber lie in the region of the inferior vena cava (Vena cava inferior), that is, before the right ventricle in the flow direction of the blood. The tube section arranged distally from the pump chamber is to extend through the right ventricle, with the result that the outlet opening is ideally arranged in the region of the pulmonary artery. In this ideal position, blood can be sucked into the catheter interior in the region of the vena cava via the inlet opening. Thereafter, the blood sucked into the catheter interior can be pumped in the distal direction (that is, through the pump chamber and the distal tube section) in order to leave the catheter in the region of the pulmonary artery (Aorta pulmonaris) via the distal outlet opening.

In the catheter state configured for use on the patient, a balloon fillable with a fluid is arranged within the pump chamber. A displacing effect of the filled balloon allows a directed transport of the blood through the catheter interior in the distal direction. The balloon is supplied with the fluid (generally a gas such as, for example, helium) from outside the catheter via a supply line guided through the tube lumen of the proximal part. The supply line ends at the proximal catheter end or protrudes therefrom. The supply line or the proximal catheter end can be connected to an (extracorporeal) pump unit. The pump unit can be controlled by means of an (integrated) control unit such that the balloon is periodically filled with the fluid. The unit composed of balloon and pressure tube can be formed by an intra-aortic balloon catheter (IAB catheter), which is known in the prior art and which is conventionally used in the so-called intra-aortic counterpulsation method. The pump unit can be formed by an IABP console (IABP=intra-aortic balloon pump) known in the prior art. Such a console is typically adjustable with respect to the frequency of filling operations to fill the balloon with fluid and/or the volume of fluid per filling operation.

Preferably, the inlet element is expandable. In the context of the invention, the property "expandable" means that the inlet element is switchable between two configurations with different inner volumes. The configuration with larger inner volume can be referred to as "expanded", and the other configuration can be referred to as "folded". In particular, the inlet element can comprise a self-expandable, that is, self-erecting, stent.

A check valve can be arranged at the inlet opening and/or in the region of the coupling section. The check valve can especially be configured as a film valve.

The inlet element can comprise a multiplicity of inlet openings.

The coupling element can be configured to transmit to the proximal section, at least proportionally, a force which acts on the distal section during implantation and/or explantation of the catheter. In particular, the inlet element and/or the pump chamber can form support structures which extend into the coupling element and mechanically stabilize it. Preferably, the support structures are extensions of the self-erecting stent and protrude into the coupling element in a web-shaped manner.

Preferably, the coupling element comprises coupling structures which engage with the support structures of the inlet element and/or with the support structures of the pump chamber in a form-fitting and/or force-fitting manner and bring about force transmission at least proportionally. Preferably, the coupling structures are produced from a nonmetallic material, especially a polymer.

Preferably, the geometric configuration of the inlet element in the expanded and in the folded configuration is harmonized with an (individual) patient's size.

BRIEF DESCRIPTION OF THE DRAWINGS

The invention will now be described with reference to the drawings wherein.

DESCRIPTION OF THE PREFERRED EMBODIMENTS OF THE INVENTION

Matching parts have identical reference signs in the different figures.

Figure 1:
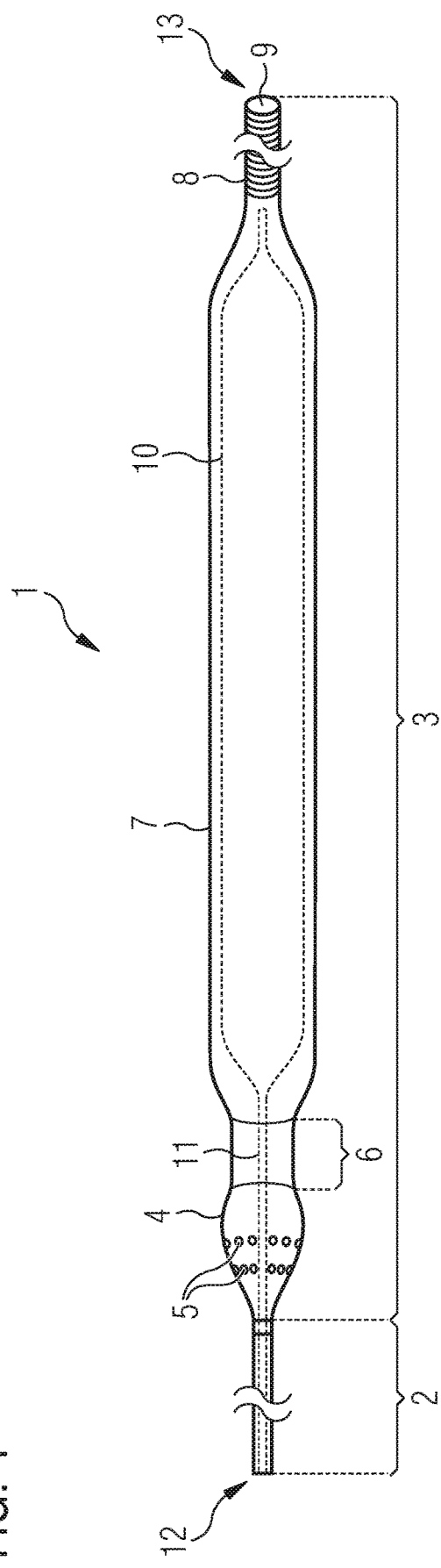
FIG. 1 shows a detail of a pump catheter having an inlet element with multiple inlet openings and a coupling element.

FIG. 1 shows a schematic of a detail of a pump catheter 1 according to the invention. Adjoining a tubular proximal section 2 is a distal section 3. The distal section 3 comprises an inlet element 4 with multiple inlet openings 5, a coupling element 6, an expandable pump chamber 7, and a tube section 8 arranged distally from the pump chamber 7 and having a distal outlet opening 9 at the distal catheter end 13. Arranged within the pump chamber 7 is a balloon 10 (dashed lines). Connected to the balloon 10 is a supply line 11 (likewise depicted as dashed) which supplies the balloon 10 with helium and runs within the catheter 1 as far as the proximal catheter end 12. The catheter 1 can preferably be used as a pump catheter for the right side of the heart. For use on the right side of the heart, the catheter 1 is led into the patient's body with the distal end 13 out in front via a body-vein opening in the groin area, specifically such that the distal tube section 8 extends through and thus bridges the right side of the heart. Ideally, the pump chamber 7 is to be placed in the region of the inferior vena cava, before the right atrium of the heart in the flow direction of the blood. A (partial) placement of the pump chamber 7 within the right atrium is alternatively possible. The supply line 11 is extracorporeally connected to a pump or pump console (not shown) which alternatingly pumps helium into the balloon 10 at a predetermined frequency, for example at about 100 bpm (beats per minute), and removes it therefrom. In this way, the balloon 10 acts according to the displacer principle as the drive for a directed transport of the blood surrounding the catheter into the catheter 1 and through the catheter 1 in the distal direction as far as the outlet opening 9. The pump chamber 7, the coupling element 6 and the inlet element 4 are sufficiently rigid to resist the suction or the negative-pressure effect of the inner balloon 10 that has just deflated. The inlet element 4 is arranged at a distance from the pump chamber 7 and has a plurality of inlet openings 5. As a result of the negative pressure generated in the catheter interior by the deflated balloon 10, blood surrounding the catheter 1 in the region of the inlet element 4 is sucked into the catheter interior through the inlet openings 5 and flows in the distal direction into the pump chamber 7. The inlet element 4 has a smaller outer diameter compared to the pump chamber 7, meaning that venous blood can circulate unimpeded between the vascular wall and the outer wall of the inlet element 4 and it is ensured that the inlet openings are freely accessible during the suck-in phase and are not sealed by the wall of the blood vessel. The coupling element 6 has an approximate length of 1 to 2 cm. This is sufficient to significantly calm the blood flow in the direction of the pump chamber. In the inflation phase of the balloon 10, the blood sucked into the catheter is displaced owing to the rise in pressure in the interior of the catheter 1. To allow a directed displacement in the distal direction in an optimal manner, a check valve 14 (cf. FIG. 4) is provided proximally from the pump chamber 7, which check valve closes as a result of the rise in pressure and blocks the inlet openings, with the result that a backflow of the blood out of the inlet openings is precluded. In other embodiments, a check valve can also be provided at each individual inlet opening.

In a further embodiment of the pump catheter according to the invention (FIG. 2), support structures 16 are provided in the region of the coupling element 6, which support structures protrude into the coupling element 6 proceeding from the inlet element 4 and from the pump chamber 7 and, in this way, mechanically stabilize the coupling element 6. The frame 15 for the inlet element 4 is (just like the frame 15 for the pump chamber 7) preferably laser-cut from a sleeve of a shape-memory alloy, for example nitinol. The geometric Z-structure of the frame 15 in conjunction with the shape-memory behavior of the frame material means that the frame 15 can, firstly, be reliably folded and thus reduced in diameter against an erection pressure—for example by slipping on a sleeve—for better handling when implanting the catheter 1 into the patient's body and explanting the catheter 1 from the patient's body and is, secondly, rigid in the erected state to the extent that the inlet element 4 and the pump chamber 7 do not collapse up to a predetermined maximum pressure difference between the inner pressure and the pressure of the surroundings.

Outside, the frame 15 of the inlet element 4 is covered with a shell film. Inlet openings 5 are fabricated into the shell film of the inlet element 4. In further embodiments, the inlet openings 5 can be provided with valves. To this end, film strips are provided between shell film and frame 15 in some embodiments. The film strips are approximately as broad as an individual inlet opening 5 and taut between shell film and frame 15 such that the inlet openings 5 are exactly covered. The film strips are connected to the shell film in a punctual manner or along lines at right angles to the film strip. What is important is that regions of the film strip are not connected to the shell film. In the event of a positive pressure within the inlet element 4, the film strip is pressed against the shell film from the inside and, in this way, blocks or seals the inlet openings 5. By contrast, what is brought about by a negative pressure in the interior of the inlet element 4 is that surrounding blood pushes through the inlet openings 5 against the film strip. The result of this is that the film strip inwardly lifts off from the shell film, meaning that the blocking action at the inlet openings 5 is neutralized. Because regions of the strip are not connected to the shell film, blood can flow into the interior of the inlet element 4 (cf. blood flow 18 in FIGS. 3, 4).

The coupling element 6 arranged between the inlet element 4 and the pump chamber 7 ensures calming of the blood flow 18 in the distal direction, this allowing an altogether gentler transport of the blood through the catheter 1. As already mentioned, the coupling element 6 is stiffened by means of the support structures 16. In some embodiments, the support structures 16 are webs which are each formed on the self-erecting frame 15 (cf. FIGS. 2, 3). Outside, the support structures 16 are, in a similar manner to the frame 15 of the inlet element 4, covered with a shell film. Like the inlet element 4, the coupling element 6 can also be "folded" or reduced in diameter by slipping on a sleeve for optimized handling with catheter-based implantation and explantation. The coupling element 6 is advantageously between 5 and 20 mm in length and has (in the erected state) an inner diameter between 5 and 15 mm.

Figure 2:
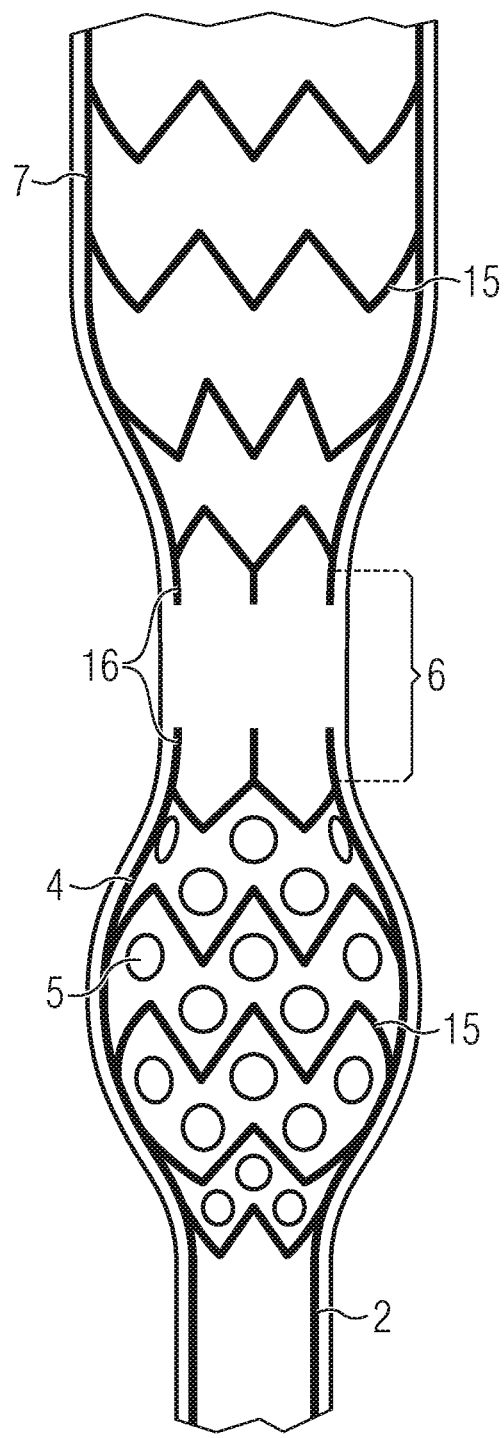
FIG. 2 shows a detail of a pump catheter having an inlet element with multiple inlet openings and support structures which extend into the coupling element.
Figure 3:
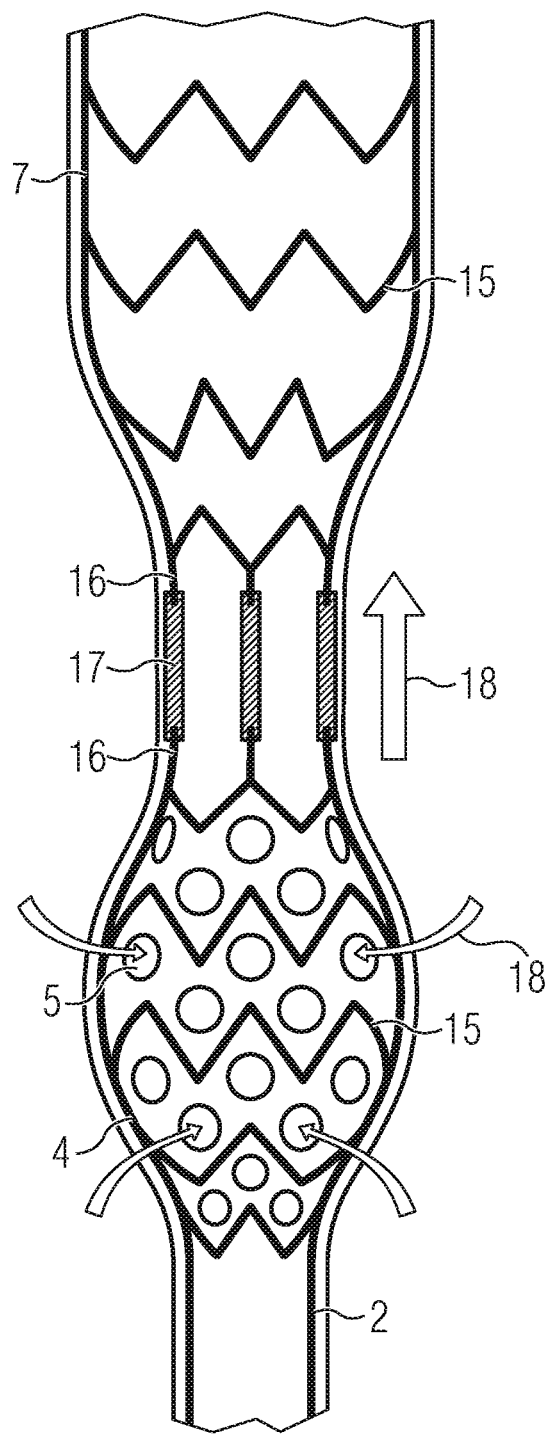
FIG. 3 shows a detail of a pump catheter having an inlet element with multiple inlet openings and support structures which extend into the coupling element and also coupling structures in the region of the coupling element; and, FIG. 4 shows a detail of a pump catheter having an inlet element with multiple inlet openings and a coupling element which has a check valve.

In the embodiment of FIG. 3, a further development of the coupling element 6 of the catheter 1 of FIG. 2 is shown. The coupling element 6 of FIG. 3 additionally has coupling structures 17. The coupling structures 17 bring about a further improved stiffening of the coupling element 6. The coupling structures 17 engage with the support structures 16. In some embodiments, the coupling structures 17 are thin rods. The rods can, for example, be composed of a body-compatible plastic or a metal. If solid rods are used, the rod ends thereof on both ends of the rods have holes into which the support structures 16 can be inserted, bonded, screwed. Hollow rods or sleeves also function in an analogous manner. In this way, a form-fitting and/or force-fitting connection is established, this further improving the handling of the catheter 1 especially during implantation and explantation.

Figure 4:
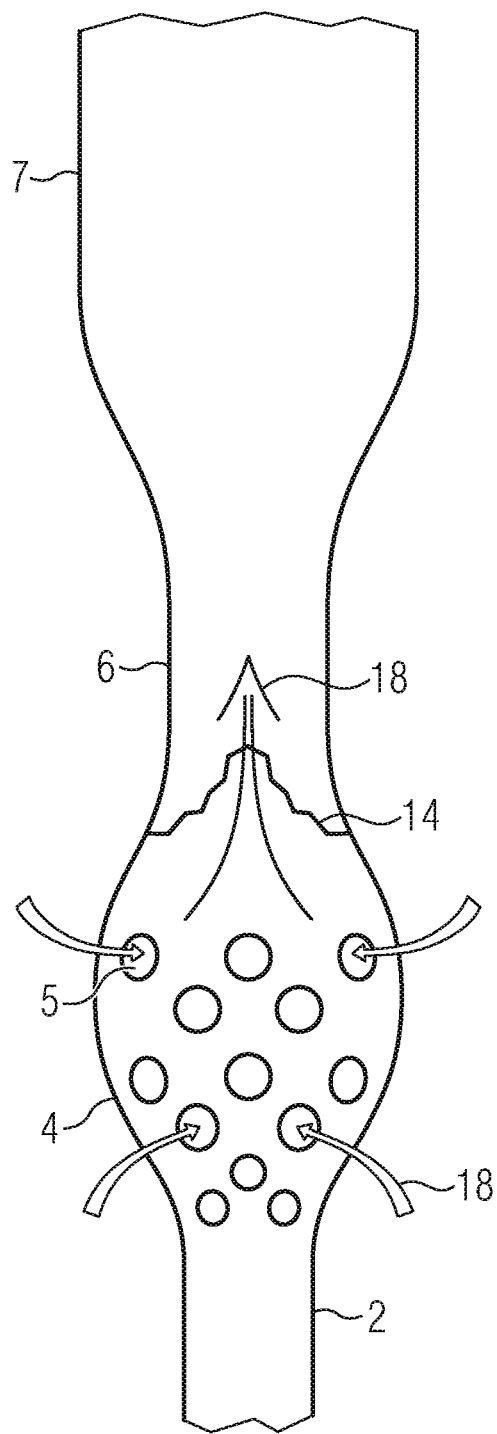

Lastly, in the embodiment of FIG. 4, the coupling element 6 of the catheter 1 according to the invention additionally comprises a valve 14. The arrangement of the valve 14 improves the directed transport of the blood in the distal direction. The valve 14 allows passage of blood in the flow direction 18 and blocks blood flow in the opposite direction. In the embodiment of FIG. 4, the valve 14 is formed by a film curtain 14 which is radially connected (bonded, welded) to the shell film of the coupling element 6 and allows passage of blood in the direction 18, but not in the opposite direction. In addition, what can be placed behind the curtain 14, seen in the flow direction 18, is a lattice (not depicted in FIG. 4 for reasons of clarity), against which the curtain 14 is pressed when blood pushes against the curtain 14 against the direction 18. The lattice can, for example, be formed by a perforated film which is likewise radially connected (bonded, welded) to the shell film of the coupling element 6 behind the curtain.

It is understood that the foregoing description is that of the preferred embodiments of the invention and that various changes and modifications may be made thereto without departing from the spirit and scope of the invention as defined in the appended claims.

LIST OF REFERENCE SIGNS

1 Pump catheter
2 Proximal section
3 Distal section
4 Inlet element
5 Inlet opening/5' Inlet valve
6 Coupling element
7 Pump chamber
8 Distal tube section
9 Outlet opening
10 Balloon
11 Supply line
12 Proximal catheter end
13 Distal catheter end
14 Check valve
15 Self-erecting frame
16 Support structure
17 Coupling structure
18 Flow direction of the blood

What is claimed is:
1. A pump catheter for the directed pulsatile conduction of blood, the pump catheter comprising:
a proximal section;
a distal section including an expandable pump chamber and a tube section disposed distally of said expandable pump chamber;
said tube section defining an outlet;
a balloon arranged within said expandable pump chamber;
said balloon being configured to be filled with a fluid;
an inlet element having at least one inlet opening and being arranged between said proximal section and said pump chamber;
a coupling element geometrically spacing said inlet element and said pump chamber from each other;

wherein only the distal section including the inlet element of the pump catheter acts as a blood pump by sucking blood into the catheter via the inlet opening and discharging it via the outlet;

wherein said blood transportation is driven by action of said balloon; and, wherein said balloon is supplied with said fluid via a supply line guided through said proximal section.

2. The pump catheter of claim 1, wherein said inlet element is expandable.

3. The pump catheter of claim 1, further comprising a check valve arranged at said inlet opening of said inlet element.

4. The pump catheter of claim 1, further comprising a check valve arranged in a region of said coupling element.

5. The pump catheter of claim 1, further comprising a first check valve at said inlet opening of said inlet element and a second check valve in a region of said coupling element.

6. The pump catheter of claim 1, wherein said inlet element includes a plurality of said inlet openings.

7. The pump catheter of claim 1, wherein said inlet element includes a plurality of inlet valves.

8. The pump catheter of claim 1, wherein a force acts on said distal section during implantation and/or explantation of said catheter into a patient's body; and, said coupling element is configured to transmit said force, at least proportionally, to said proximal section.

9. The pump catheter of claim 8, wherein at least one of said inlet element and said pump chamber form support structures which extend into said coupling element to mechanically stabilize said coupling element.

10. The pump catheter of claim 9, wherein said coupling element includes coupling structures which engage said support structures of at least one of said inlet element and said pump chamber to effect a force transmission at least proportionally.

11. The pump catheter of claim 10, wherein said coupling structures include a non-metallic material.

12. The pump catheter of claim 11, wherein said non-metallic material is a polymer.

13. The pump catheter of claim 1, wherein said inlet element has a spatial configuration of spatial-geometric extent which is coordinated with the anatomy of a patient.

* * * * *